United States Patent [19]
Sirbola

[11] Patent Number: 5,356,387
[45] Date of Patent: Oct. 18, 1994

[54] NEEDLE GUARD ASSEMBLY WITH DRAWSTRING FOR A SYRINGE

[76] Inventor: Michael Sirbola, 4468 W. Glen Pl., Rapid City, S. Dak. 57702

[21] Appl. No.: 867,419

[22] Filed: Apr. 13, 1992

[51] Int. Cl.$^5$ .................................. A61M 5/32
[52] U.S. Cl. ........................... 604/198; 604/263
[58] Field of Search ............ 604/110, 192, 198, 263

[56] References Cited

U.S. PATENT DOCUMENTS

| | | | |
|---|---|---|---|
| 4,139,009 | 2/1979 | Alvarez | 604/198 |
| 4,693,257 | 9/1987 | Markham | 128/752 |
| 4,846,809 | 7/1989 | Sims | 604/198 |
| 4,883,469 | 11/1989 | Glazier | 604/192 |
| 4,892,521 | 1/1990 | Laico et al. | 604/192 |
| 4,978,344 | 12/1990 | Dombrowski et al. | 604/198 |
| 4,998,922 | 3/1991 | Kuracina et al. | 604/192 |
| 5,013,305 | 5/1991 | Opie et al. | 604/192 |
| 5,108,379 | 4/1992 | Dolgin et al. | 604/198 |

FOREIGN PATENT DOCUMENTS

| | | | |
|---|---|---|---|
| 2625103 | 6/1989 | France | 604/198 |

OTHER PUBLICATIONS

"The First Line of Defense Against Needle Stick Injuries: Introducing the ICU HR Needle", flyer, undated.

*Primary Examiner*—John D. Yasko
*Assistant Examiner*—Adam J. Cermak
*Attorney, Agent, or Firm*—Harrison & Egbert

[57] ABSTRACT

A needle guard for a syringe having a forward annular member with an internal diameter sufficient to extend around a diameter of a syringe needle, a cap flexibly fastened to the forward annular member, a rearward annular member having a diameter suitable for attachment to the syringe, and a resilient member connected to the rearward annular member and connected to the forward annular member so as to urge the forward annular member away from the rearward annular member. The cap is fastened to an end of the forward annular member opposite said resilient member. The cap is movable from a first position in proximity to an end of the forward annular member and a second position away from the end of the forward annular member. A drawstring is connected at one end to the forward annular member and extends toward the rearward annular member so as to actuate a movement of the forward annular member toward the rearward annular member.

16 Claims, 2 Drawing Sheets

NEEDLE GUARD ASSEMBLY WITH DRAWSTRING FOR A SYRINGE

TECHNICAL FIELD

The present invention relates to needle guards for syringes. More particularly, the present invention relates to needle guard assemblies which are attached to the syringe.

BACKGROUND ART

Hypodermic needles are in common use today on syringes, catheters, and related devices. They are used for subcutaneous injection, the taking of blood samples, the intravenous administration of medicines, biopsies, and other medical procedures. The needles are usually supplied in sterilized individual packages and are meant to be used once and then disposed of, although some needles are meant to be re-used after sterilization. A single use of a hypodermic needle renders it non-sterile and septic, and potentially contaminated by bloodborne diseases which may be present in the patient. Such contamination can includes AIDS, hepatitis, veneral disease, and other blood-borne diseases.

A hypodermic needle has a sharp end for the purpose of penetrating the human body. A major source of injury and infection to health care workers has been the accidental sticks and jabs by septic, used hypodermic needles. The accidental penetration of the body by these jabs causes a deep puncture wound. A stab by a needle that has been used in an infected patient can spread the patient's infection to the health care worker. The major cause of the spread of the AIDS epidemic and the hepatitis epidemic to health care workers has been the accidental stabs of these workers by previously used, contaminated needles.

This problem is often aggravated by the fact that disposal of medical debris is often made in modern plastic garbage bags. These garbage bags are easily punctured by the disposable, contaminated hypodermic needle. Accidental stabbings can occur to the maintenance personnel or other personnel involved in the disposal of medical refuse.

Some attention has been given to developing guards for hypodermic needles to protect from accidental needle stabs. U.S. Pat. No. 3,688,396, to Smith, and U.S. Pat. No. 3,612,302 to Burke and Raines, show needles with caps over them. Although the caps, once in place, will protect from needle stabs, the act of placing the caps over the needles places the fingers holding the cap in front of the tip of the needle. While inserting the tip of the needle into the cap, a "near miss" can stab the fingers holding the cap. Capping the needle may place the health care worker in more danger of accidental needle stabs than if the needle were disposed of without a cap at all.

U.S. Pat. No. 4,329,989, issued to Dallons et al., shows a cap attached to the needle assembly. This provides for convenience in preventing the misplacement of the cap, but does nothing to keep the fingers from being in front of the needle tip when applying the cap. Once again, this patent shows a misconception. This misconception is that needle jabs will be prevented by placing a cap over the end of the needle. In actuality, many of these accidental stabbings occur during the process of placing such a safety cap over the hypodermic needle.

U.S. Pat. No. 4,623,336, issued to Pedicano et al., shows a needle guard cap that requires that fingers be in front of the tip of the needle to apply the cap, but the cap has a large flange guard to protect the fingers when inserting the needle into the cap. Unfortunately, the resulting cap is large, cumbersome, relatively expensive, and is not part of an integrated needle assembly. This cap is not in common use in the medical profession.

A device for the prevention of accidental needle stick injuries has been developed and introduced by ICU Medical, Inc. of Mission Viejo, Calif. This device is a pop-up needle guard. This guard has an open end that allows the health care worker to inject the patient with the needle. Unfortunately, this open end can "pop-down" or "pop-off" to expose the tip of the needle, after the guard is "popped-up" following injection. A simple inadvertent wiggling manipulation of the device can cause this inadvertent "pop-down" or "pop-off". This wiggling is facilitated by the fact that the diameter of the guard must be larger than that of the needle, especially at the open end of the guard. Also a simple hard jamming motion on the tip of the guard after it is "popped-off" can cause it to "pop-down", exposing the needle. Also, this needle guard assembly must have two moving parts assembled together. The snap-lock portion requires precise engineering, manufacture and assembly. This is an extremely costly feature in relation to the cost of the hypodermic needle itself, and deters widespread use.

It is an object of the present invention to provide a guard for hypodermic needles to prevent accidental needle stab injuries by previously used, septic, hypodermic needle.

It is another object of the present invention to prevent puncture wounds and the spread of infectious disease to health care workers and others.

It is still another object of the present invention to provide such a guard that can be positioned over a used needle without requiring the fingers of the health care worker to be placed in front of the tip of the needle.

It is another object of the present invention to provide such a guard with a closed end over the tip of the needle so that an accidental jabbing motion will not cause the guard to "pop-down" and again expose the top of the needle.

It is a further object of the present invention to provide such a guard assembly as part of an integrated needle assembly capable of inexpensive manufacture, compact size, convenient use, and reliability.

It is still another object of the present invention to provide a means by which a hospital or other health care facility can accommodate the desires of its medical service personnel to reduce the risks to them of injury from needle stabs and infection by AIDS and other blood-borne diseases.

These and other objects and advantages of the present invention will become apparent from a reading of the attached specification and appended claims.

SUMMARY OF THE INVENTION

The present invention is needle guard for a syringe which comprises a forward annular member having an internal diameter sufficient to extend around a diameter of a syringe needle, a cap flexibly fastened to the forward annular member, a rearward annular member having a diameter suitable for attachment to the syringe, and a resilient member connected to the rearward annular member and connected to the forward annular member. The resilient member urges the forward annular member away from the rearward annular member. The cap is fastened to an end of the forward annular member opposite the rearward annular member.

The cap is movable between a first position in proximity to an end of the forward annular member and a second position away from the end of the forward annular member. The cap is generally a flat member having a structural integrity suitable for preventing the syringe needle from passing therethrough when the cap is in the first position. The flat member is connected by a resilient strip to the forward annular member. The resilient strip urges the flat member to the first position. The forward annular member has a cylindrical configuration suitable for slidable relationship with the exterior surface of a syringe needle.

The resilient strip of the needle guard assembly of the present invention has a first section of a polymeric material and a second section of a similar polymeric material. Each of the first and second sections connects the forward annular member to the rearward annular member. These first and second sections define a needle-receiving passageway therebetween. The sections of polymeric material are configured so as to bow outwardly with respect to the passageway when the forward annular member is moved toward the rearward annular member.

The present invention also includes a suitable drawstring connected at one end to the forward annular member. The drawstring extends toward the rearward annular member. This drawstring is suitable for actuating a movement of the forward annular member toward the rearward annular member. The drawstring comprises a flexible line connected at one end to the forward annular member, and a guide connected to the syringe so as to receive the flexible line therein. A button is connected to the end of the flexible line opposite the forward annular member. The button causes the lnie to pull the forward annular member toward the rearward annular member.

DETAILED DESCRIPTION OF THE INVENTION

Figure 1:
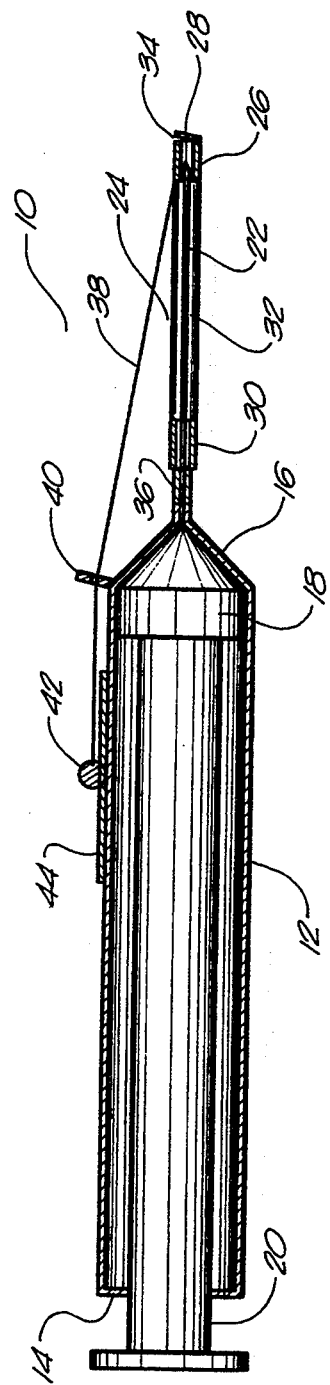
FIG. 1 is a cross-sectional view in side elevation of the needle guard assembly of the present invention, showing the needle guard assembly in its protective position.

Referring to FIG. 1, there is shown at 10, a syringe in accordance with the preferred embodiment of the present invention. Syringe 10 includes a barrel 12 having one open end 14 and one closed end 16, a piston 18 slidably positioned within barrel 12, a shaft 20 extending beyond the open end 14 of barrel 12, a hypodermic needle 22 connected to and communicating with the restricted end 16 of barrel 12, and a guard assembly 24 fastened to the hypodermic needle 22. The principal feature of the present invention is the arrangement and configuration of guard assembly 24, alone, and in combination with syringe 10.

Generally, the syringe 10 is a standard, commercially available syringe. The piston 18 forms a liquid-tight seal with the interior of barrel 12. Shaft 20 extends beyond the open end 14 of barrel 12 and acts as a plunger relative to piston 18. The hypodermic needle 22 is attached to the restricted end 16 of barrel 12 through standard means, such as a LUER(TM). It should be noted that the guard assembly 24 can be used in combination with a standard syringe, as shown in FIG. 1, and with various other types of syringes.

In FIG. 1, guard assembly 24 can be seen as having a forward annular member 26, a cap 28, a rearward annular member 30, and a resilient strip 32. The forward annular member 26 has an internal diameter sufficient to extend around the diameter of the hypodermic needle 22. In general, the forward annular member 26 has a cylindrical configuration suitable for slidable relationship with the needle 22.

The cap 28 is flexibly fastened to the end of the forward annular member 26. The cap 28 is movable between a first position, as shown in FIG. 1, in proximity to an end 34 of the forward annular member 26 and a second position away from the end 34 of forward annular member 26. As can be seen, the cap 28 is a generally flat member having a structural integrity suitable for preventing the syringe needle 22 from passing through the cap 28 when the cap is in the first position in proximity to the end 34 of the forward annular member 26. As will be described hereinafter, the flat member 28 is connected by a resilient strip to the forward annular member 26. The resilient strip tends to urge the flat member 28 into the position illustrated in FIG. 1.

The rearward annular member 30 is a section of material which is affixed to an exterior surface of the needle 22. As can be seen in FIG. 1, the rearward annular member 30 is affixed adjacent to the LUER(TM) lock 36 between the syringe body 12 and the hypodermic needle 22. The rearward annular member can be affixed to needle 22 by various adhesive or sealing techniques. In general, the rearward annular member 30 has an interior diameter suitable for attachment to the exterior of the needle 22 or to another exterior portion of the syringe.

The resilient member 32 is connected at one end to the rearward annular member 30 and is connected at the other end to the forward annular member 26. The resilient member 32 is designed so as to urge the forward annular member 26 away from the rearward annular member 30. In this fully extended position, as shown in FIG. 1, the forward annular member 26 extends outwardly beyond an end of the needle 22. The resilient member 32 is a tubular section of polymeric material which is formed of two generally symmetrical portions which surround the outer diameter of needle 22. The interior of the resilient member 32 defines a passageway through which the needle 22 extends.

The needle guard assembly 24 of the present invention further includes a drawstring 38 which is connected at one end to the forward annular member 26 and extends rearwardly therefrom. Drawstring 38 serves to actuate a movement of the forward annular member 26 toward the rearward annular member 30. The drawstring 38 is essentially a flexible line that has one end connected to the forward annular member 26. A guide member 40 is fastened to the syringe body 12 so as to form a pathway for the drawstring 38. The guide 40 has a central opening so as to allow the drawstring 38 to extend therethrough. A button 42 is fastened to the end of the drawstring 38 opposite the forward annular member 26. Button 42 has a diameter which prevents passage through the opening of guide 40. The button 42 has a generally spherical shape which is received by track 44 formed on the outer diameter of syringe body 12. The movement of the button 42 of the drawstring allows the user of the syringe 10 to properly actuate the guard assembly 24 so as to enable the use of the hypodermic needle 22 of the syringe 10.

Figure 2:
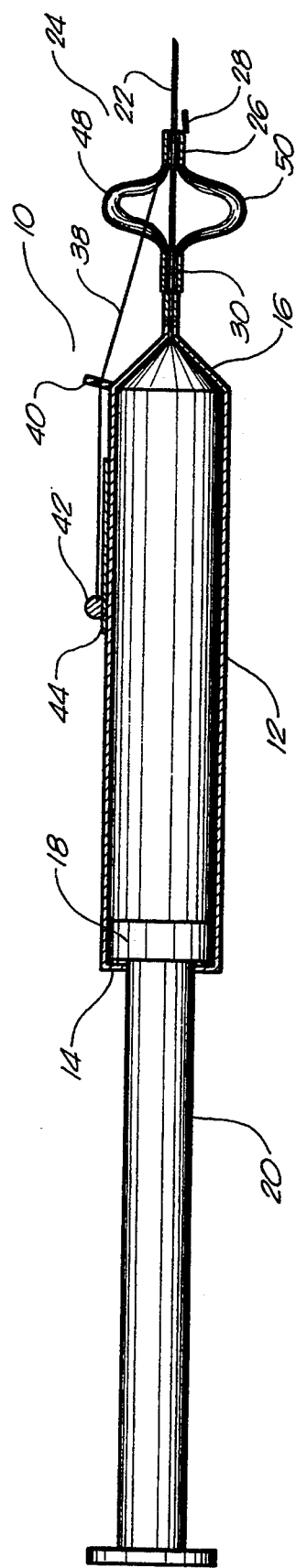
FIG. 2 is a cross-sectional view of the syringe of the present invention showing the needle guard assembly in its retracted position.

FIG. 2 shows the operation of the guard assembly 24 of the present invention. In order to expose the needle 22 for use, it is necessary for the user of the syringe 10 to pull on the button 42 connected to drawstring 38. The track 44 provides a guide surface for the button 42. As the button 42 is pulled back, toward the open end 14 of syringe 10, the drawstring 38 is also pulled backward through the guide 40. This causes a concomittant movement of the forward annular member 26 of the guard assembly 24. The rearward annular member 30 remains fixed in its position at the rearward portion of the needle 22.

When the forward annular member 26 is moved rearwardly along the needle 22, the resilient member 32 flexes so as to permit the rearward movement of the forward annular member 26 along needle 22. It can be seen that the resilient member 32 includes a first section of polymeric material 48 and a second section of polymeric material 50. Each of these sections 48 and 50 has a generally semi-circular cross-section. Each of the ends of these sections 48 and 50 are connected to the forward annular member 26 and the rearward annular member 30. When the drawstring 38 causes a retraction of the forward annular member 26 along needle 22, the sections 48 and 50 bow outwardly from the position shown in FIG. 1. As such, sections 48 and 50 provide resistance to the rearward movement of the forward annular member 26. It should be understood that the ends of sections 48 and 50 can form the rearward annular member 30.

Importantly, as the forward annular member 26 is moved rearwardly on needle 22, the cap 28 opens to its second position. It can be seen that the cap 28 assumes a position that is angularly removed from the end 34 of the forward annular member 26. This allows the sharp end of needle 22 to pass outwardly from the forward annular member 26.

After the needle 22 has been inserted into either a patient or through the rubber cap of a medicine vial, the button 42 of drawstring 38 can be released. The shaft 20 can then be used to inject or to withdraw fluids. It is not necessary to hold the drawstring 38 after the needle is inserted. The resilient member 32 causes the forward annular member 26 to move back toward the end of needle 22. After the forward annular member 26 extends beyond the end of the needle 22, the cap 28 automatically flexes back to the position shown in FIG. 1.

Figure 3:
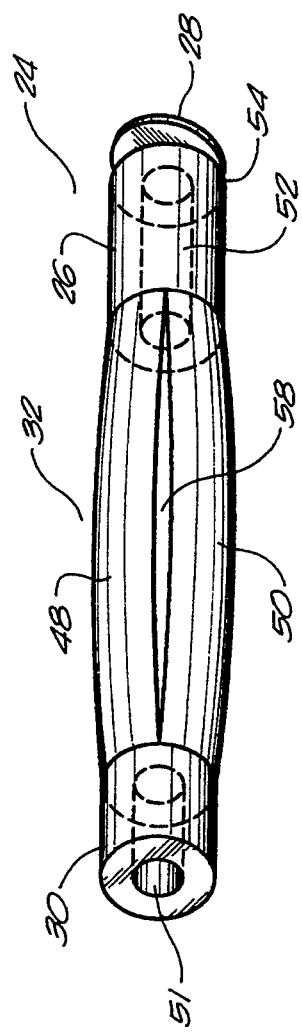
FIG. 3 is a perspective view of the needle guard assembly of the present invention.

FIG. 3 is an isolated view of the guard assembly 24 of the present invention. Guard assembly 24 shows the forward annular member 26, the cap 28, the rearward annular member 30, and the resilient member 32. It can be seen that the rearward annular member 30 includes a central opening 51 which is slidable over the exterior diameter of the needle so as to be positioned adjacent to the luer lock of the syringe. The central opening 51 of the rearward annular member 30 can include a suitable adhesive, or other material, so as to fix the annular member 30 in its proper position on the needle.

The central opening 52 of the forward annular member 26 is sized so as to fit over the exterior diameter of the needle. The central opening 52 allows the needle to slide freely therethrough. The cap 28 is hinged at 54 to the end of the forward annular member 26. The resilient member 32 is comprised of a first section 48 and a second section 50 of flexible polymeric material. In simple terms, the resilient member 32 can comprises a flexible plastic tube which includes a slit 58 extending therethrough. The natural resiliently of such a tube will create the forces in the sections 48 and 50 so as to urge the forward annular member 26 toward the sharp end of the syringe needle.

Figure 4:
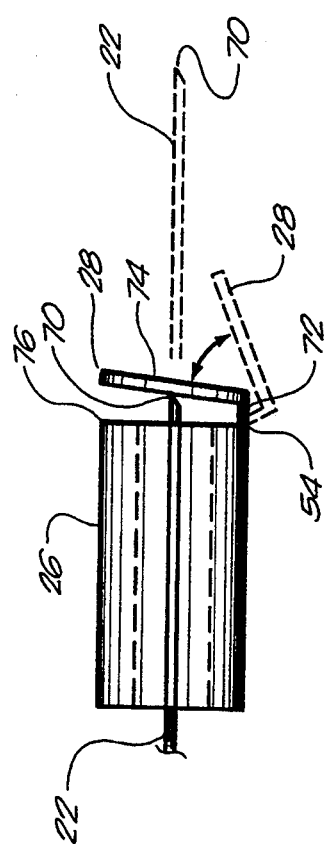
FIG. 4 is a side elevational view showing the operation of the end cap associated with the needle guard assembly of the present invention.

FIG. 4 illustrates the manner in which the cap 28 function so as to expose and to protect the needle 22 at the end of the forward annular member 26. It can be seen that the needle 22 (as shown in solid lines) extends into the forward annular member 26. In the natural storage position, the needle 22 will be contained inwardly within the body of annular member 26. FIG. 4 illustrates the situation in which it is intended to expose the end 70 of the needle 22. FIG. 4 also shows how the cap 28 protects against accidental needle stabs.

The cap 28 is initially connected to the point 54 of the forward annular member 26 by way of a resilient strip 72. Resilient strip 72 is suitable for urging the cap 28 into the position shown in solid lines of FIG. 4. In this position, the cap 28 acts as a barrier between the sharp end 70 of needle 22 and the exterior environment. As such, any contact with the back surface 74 of the cap 28 will keep the sharp end 70 of needle 22 from stabbing. The cap 28 should have a structural integrity sufficient to keep the sharp end 70 of needle 22 from penetrating the material of cap 28. Cap 28 specifically acts to block any accidental stabs with needle 22.

When it is desired to use the needle 22, the forward annular member 26 is retracted in the manner described hereinbefore. When the forward annular member is retracted, the sharp end 70 of needle 22 will abut the inner surface of the cap 28. As the forward annular member 26 continues to extend further outwardly from the end 76 of forward annular member 26, it will tend to "push" the cap 28 away from the sharp end 70 of needle 22. Eventually, the needle 22 will extend outwardly from the end surface 76 of forward annular member 26 in the manner shown in dotted line fashion in FIG. 4. The cap 28 will be flexibly extended about point 54 so as to allow the sharp end 70 of needle 22 to extend therethrough. It can be seen that the cap 28 (as shown in dotted line fashion) is removed from its blocking position. As the needle 22 is retracted toward the interior of forward annular member 26, the cap 28 will reassume the position shown in solid lines.

The present invention offers a superior technique for the prevention of needle stabs. The retention of the end of the needle within the area of the forward annular member generally prevents any accidental needle stabs from the side. The use of the flexible cap 28 prevents any accidental needle stab injuries from occurring by an encounter with the very end of the needle guard assembly. Since the cap is of a solid material, the sharp end of the needle cannot penetrate the cap so as to cause a needle stab.

When it is necessary to operate the syringe for the purpose of giving an injection, the cap is automatically displaced so as to allow the needle to extend therethrough. This can only occur by the pulling of the forward annular member rearwardly along the needle surface. The configuration of the resilient member 32 and the resilient connection between the cap 28 and the forward annular member 26 enhances the ability of the present invention to operate as an automatic stab-proof needle guard assembly.

The configuration of the present invention is relatively easy to manufacture. The device can be made of conventional materials. Additionally, and very importantly, the needle guard assembly 24 can be retrofitted to existing syringes. The present invention does not require complex manufacturing operations for the purpose of installation. The needle guard assembly of the present invention can be easily used by health care workers during injection proceedings.

It should be kept in mind that, as an alternative embodiment, the drawstring 38 can be interconnected to the shaft 20 of the piston so that a retraction of the needle guard assembly occurs simultaneously with the rearward movement of the plunger. In this manner, the needle guard assembly automatically operates so as to expose and seal the hypodermic needle.

The foregoing disclosure and description of the invention is illustrative and explanatory thereof. Various changes in the details of the illustrated construction may be made within the scope of the present invention without departing from the true spirit of the invention. The present invention should only be limited by the following claims and their legal equivalents.

I claim:

1. A needle guard for a syringe comprising:
   a forward annular member having an internal diameter sufficient to extend around a diameter of a syringe needle;
   a cap flexibly fastened to said forward annular member;
   a rearward annular member having a diameter suitable for attachment to the syringe;
   a resilient member connected to said rearward annular member and connected to said forward annular member, said resilient member for urging said forward annular member away from said rearward annular member, said cap fastened to an end of said forward annular member opposite said rearward annular member; and
   a drawstring means connected at one end to said forward annular member, said drawstring means extending toward said rearward annular member, said drawstring means for actuating a movement of said forward annular member toward said rearward annular member.

2. The needle guard of claim 1, said cap movable between a first position in proximity to an end of said forward annular member and a second position away from said end of said forward annular member.

3. The needle guard of claim 2, said cap being a generally flat member having a structural integrity suitable for preventing the syringe needle from passing therethrough when said cap is in said first position.

4. The needle guard of claim 3, said flat member fastened by a resilient connector connected to said forward annular member, said resilient connector for urging said flat member to said first position.

5. The needle guard of claim 1, said forward annular member having a cylindrical configuration suitable for slidable relationship with said syringe needle.

6. The needle guard of claim 1, said resilient member comprising:
   a first section of polymeric material; and
   a second section of polymeric material, each of said first and second sections connecting said forward annular member to said rearward annular member, said first and second sections defining a needle-receiving passageway therebetween.

7. The needle guard of claim 6, said first and second sections of polymeric material configured so as to bow outwardly with respect to said passageway when said forward annular member is moved toward said rearward annular member.

8. The needle guard of claim 1, said drawstring means comprising:
   a flexible line connected at one end to said forward annular member.

9. The needle guard of claim 8, said drawstring means further comprising:
   a button connected to an end of said flexible line opposite to said forward annular member, said button for causing said line to pull said forward annular member toward said rearward annular member.

10. An improved syringe of the type having a syringe body and a needle attached to the syringe body, the improvement comprising:
    a forward annular member slidably positioned on the needle;
    a cap resiliently fastened to an end of said forward annular member, said cap movable between an open position and a closed position with respect to said forward annular member;
    attachment means for fastening to the syringe body;
    a resilient member connected at one end to said attachment means and at another end to said forward annular member, said resilient member for urging said forward annular member toward an end of the needle; and
    means for moving said forward annular member from the position at said end of said needle, said means for moving comprising a drawstring connected at one end to said forward annular member, said drawstring extending toward the syringe body.

11. The improvement of claim 10, said cap being in said closed position when said forward annular member is at said end of the needle, said closed position for preventing said needle from passing through said cap.

12. The improvement of claim 10, said cap connected by a resilient connector to said forward annular member, said resilient connector for urging said cap into said closed position.

13. The improvement of claim 10, said attachment means comprising:
    a rearward annular member fastened to a needle assembly of the syringe.

14. The improvement of claim 10, said resilient member comprising:
    a first strip of flexible material; and
    a second strip of flexible material, each of said first and second strips connecting said attachment means to said forward annular member, said first and second strips defining a passageway therebetween, the needle extending through said passageway.

15. The improvement of claim 10, said means for moving further comprising:

a guide connected to the syringe body, said guide for receiving said drawstring, said guide providing said drawstring with a pathway of travel.

16. A needle guard for a syringe comprising:

a forward annular member having an internal diameter sufficient to extend around a diameter of a syringe needle;

an attachment member having means thereon for attachment to the syringe;

a resilient member connected to said attachment member and to said forward annular member, said resilient member for urging said forward annular member away from said attachment member;

a drawstring means connected to said forward annular member and extending rearwardly therefrom, said drawstring means for actuating a movement of said forward annular member toward said attachment means; and a guide means interconnected to said attachment means, said guide means receiving said drawstring means, said guide means providing a pathway of travel for said drawstring means.

* * * * *